(12) United States Patent
Gu et al.

(10) Patent No.: US 10,487,021 B2
(45) Date of Patent: Nov. 26, 2019

(54) CATALYSTS SUPPORTED ON MODIFIED-CARRIER FOR OXIDATIVE COUPLING REACTION OF METHANE AND METHOD FOR OXIDATIVE COUPLING REACTION OF METHANE USING THE SAME

(71) Applicant: KOREA INSTITUTE OF SCIENCE AND TECHNOLOGY, Seoul (KR)

(72) Inventors: Sangseo Gu, Seoul (KR); Jeong-Myeong Ha, Seoul (KR); Jae Wook Choi, Seoul (KR); Dong Jin Suh, Seoul (KR); Young Hyun Yoon, Seoul (KR); Jungho Jae, Seoul (KR); Jung Kyu Choi, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 0 days.

(21) Appl. No.: 15/857,541

(22) Filed: Dec. 28, 2017

(65) Prior Publication Data
US 2019/0152876 A1    May 23, 2019

(30) Foreign Application Priority Data

Nov. 20, 2017 (KR) .................. 10-2017-0155066

(51) Int. Cl.
*C07C 2/84* (2006.01)
*B01J 29/04* (2006.01)
(Continued)

(52) U.S. Cl.
CPC ............. *C07C 2/84* (2013.01); *B01J 21/08* (2013.01); *B01J 23/34* (2013.01); *B01J 29/041* (2013.01);
(Continued)

(58) Field of Classification Search
CPC . C07C 2/84; C07C 2523/30; C07C 2529/035; C07C 2529/48; C07C 2529/78;
(Continued)

(56) References Cited

U.S. PATENT DOCUMENTS 6,518,476 B1    2/2003 Culp et al.
6,596,912 B1    7/2003 Lunsford et al.
(Continued)

FOREIGN PATENT DOCUMENTS

CN    103657640 B    9/2015
EP    2576046 B1    11/2014
(Continued)

OTHER PUBLICATIONS

Translation of WO-2015101345-A1 (Year: 2015).*
(Continued)

*Primary Examiner* — Philip Y Louie
*Assistant Examiner* — Ali Z Fadhel
(74) *Attorney, Agent, or Firm* — Cantor Colburn LLP

(57) ABSTRACT

The present disclosure relates to catalysts supported on a modified-carrier for oxidative coupling reaction of methane and a method for oxidative coupling reaction of methane using the same. The catalysts in which sodium tungstate is supported on a delaminated zeolite carrier increase the methane conversion rate and the selectivity to $C_{2+}$ hydrocarbon compounds and thereby improve the reactivity of the oxidative coupling reaction of methane.

12 Claims, 2 Drawing Sheets

(51) Int. Cl.
   *B01J 29/70* (2006.01)
   *B01J 29/40* (2006.01)
   *B01J 23/34* (2006.01)
   *B01J 21/08* (2006.01)

(52) U.S. Cl.
   CPC .............. *B01J 29/40* (2013.01); *B01J 29/70* (2013.01); *B01J 29/7038* (2013.01); *C07C 2521/08* (2013.01); *C07C 2523/30* (2013.01); *C07C 2523/34* (2013.01); *C07C 2529/035* (2013.01); *C07C 2529/40* (2013.01); *C07C 2529/48* (2013.01); *C07C 2529/70* (2013.01); *C07C 2529/78* (2013.01)

(58) Field of Classification Search
   CPC ............ C07C 2521/08; C07C 2529/70; C07C 2529/40; C07C 2523/34; B01J 21/08; B01J 23/34; B01J 29/40; B01J 29/70; B01J 29/7038; B01J 29/041
   See application file for complete search history.

(56) References Cited

U.S. PATENT DOCUMENTS

| | | | |
|---|---|---|---|
| 7,902,113 | B2 | 3/2011 | Zarrinpashne et al. |
| 8,129,305 | B2 | 3/2012 | Bagherzadeh et al. |
| 2007/0293709 | A1 | 12/2007 | Iaccino et al. |
| 2013/0178680 | A1 | 7/2013 | Ha et al. |
| 2014/0080699 | A1 | 3/2014 | Ghose et al. |
| 2014/0274671 | A1 | 9/2014 | Schammel et al. |
| 2016/0023962 | A1* | 1/2016 | Henao ................. C07C 2/84 585/417 |

FOREIGN PATENT DOCUMENTS

| | | |
|---|---|---|
| EP | 2853521 A1 | 4/2015 |
| JP | 2009534382 A | 9/2009 |
| JP | 5493928 B2 | 5/2014 |
| KR | 100999368 B1 | 12/2010 |
| KR | 1020100130722 A | 12/2010 |
| KR | 101039604 B1 | 6/2011 |
| KR | 101294592 B1 | 8/2013 |
| KR | 1020150087557 A | 7/2015 |
| WO | 2007126811 A2 | 11/2007 |
| WO | 2011149996 A2 | 12/2011 |
| WO | 2015057753 A1 | 4/2015 |
| WO | WO-2015101345 A1 * | 7/2015 ............... C07C 2/84 |

OTHER PUBLICATIONS

Corma et al., "Delaminated zeolite precursors as selective acidic catalysts", Letters to Natura, Nature, vol. 396, Nov. 26, 1998, p. 353-356. (Year: 1998).*

Diaz, Review Article: "Layered Materials with Catalytic Applications: Pillared and Delaminated Zeolites from MWW Precursors", International Scholarly Research Network, ISRN Chemical Engineering, vol. 2012, Article ID 537164, 35 pages. (Year: 2012).*

Baerlocher et al., "Atlas of Zeolite Framework Types", 2007, pp. 1-398, 6th Revised Edition, Elsevier B.V.

Leonowicz et al., "MCM-22: A Molecular Sieve with Two Independent Multidimensional Channel Systems", Science, Jun. 24, 1994, pp. 1910-1913, vol. 264.

Miguel A. Camblor et al., "A New Microporous Polymorph of Silica Isomorphous to Zeolite MCM-22", Chemistry of Materials, 1996, pp. 2415-2417, vol. 8, American Chemical Society.

Miguel A. Camblor et al., "Synthesis and Structural Characterization of MWW Type Zeolite ITQ-1, the Pure Silica Analog of MCM-22 and SSZ-25", Journal of Physical Chemistry B, 1998, pp. 44-51, vol. 102, No. 1, American Chemical Society.

Sudeep Maheshwari et al., "Layer Structure Preservation during Swelling, Pillaring, and Exfoliation of a Zeolite Precursor", Journal of the American Chemical Society, Jan. 8, 2008, pp. 1507-1516, vol. 130, No. 4.

Y. J. He et al., "Synthesis, characterization and catalytic activity of the pillared molecular sieve MCM-36", Microporous and Mesoporous Materials, 1998, pp. 207-224, vol. 25.

* cited by examiner

CATALYSTS SUPPORTED ON MODIFIED-CARRIER FOR OXIDATIVE COUPLING REACTION OF METHANE AND METHOD FOR OXIDATIVE COUPLING REACTION OF METHANE USING THE SAME

CROSS-REFERENCE TO RELATED APPLICATION

This application claims the priority of Korean Patent Application No. 10-2017-0155066, filed on Nov. 20, 2017, and all the benefits accruing therefrom under 35 U.S.C. § 119, the contents of which in its entirety are herein incorporated by reference.

BACKGROUND OF THE INVENTION

Field of the Invention

The present disclosure relates to catalysts supported on a modified-carrier for oxidative coupling reaction of methane and a method for oxidative coupling reaction of methane using the same.

This research was conducted with the support of the Ministry of Science and ICT under the supervision of the Korea Institute of Science and Technology (specialized organization for research management: National Research Foundation of Korea, project title: Development of Technology of Catalysts for Preparation of Olefin through Oxidative Coupling Reaction of Methane, project number: 1711035471).

Also, this research was conducted with the support of the Ministry of Science and ICT under the supervision of the Korea Institute of Science and Technology (specialized organization for research management: National Research Foundation of Korea, project title: Project for Development of Fundamental Technology of Carbon Cycle Utilization, project number: 2016U00034).

Description of the Related Art

Although methane is very abundant in nature, researches on the conversion of methane have faced difficulties due to its high chemical stability. However, methane has a very high potential. Since it consists of one carbon, it can be converted to a higher value hydrocarbon by linking a carbon chain thereto.

Therefore, the technology for increasing the added value of methane is under active research. Methane conversion technology can be divided into direct conversion technology and indirect conversion technology. The indirect conversion technology is a technology of converting methane to a hydrocarbon with a longer carbon chain using a multistage reaction. In this technology, a synthesis gas is first produced by the reforming of methane, and the synthesis gas produced is further processed to extend the carbon chain. This method is currently partially commercialized, but it has a problem that it requires large energy consumption and high initial investment costs. The direct conversion technology of methane is being studied to solve various problems of the indirect conversion technology of methane. The direct conversion technology of methane has the advantage of linking the carbon chains of methane with a single process. However, it still has limitations in economic feasibility. Therefore, many technologies are being studied to solve these problems.

One of the direct conversion technologies of methane is the oxidative coupling reaction of methane. In this method, methane is converted to methyl radicals, which are coupled to each other to produce a $C_2$ hydrocarbon, and the $C_2$ hydrocarbon is subjected to an additional oxidation reaction to obtain a $C_{2+}$ hydrocarbon. The reaction is shown in Scheme 1 below.

<Scheme 1>

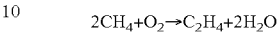

$$2CH_4 + O_2 \rightarrow C_2H_4 + 2H_2O$$

With the oxidative coupling reaction of methane, it is possible to convert methane to a $C_{2+}$ hydrocarbon using a single process, but its economic feasibility has not yet reached the level of commercialization. Thus, it is necessary to develop a catalyst for improving the methane conversion rate and the selectivity to $C_{2+}$ hydrocarbon, and even a small increase of the methane conversion rate and the selectivity to $C_{2+}$ hydrocarbon involves a lot of technical difficulties.

SUMMARY OF THE INVENTION

One aspect of the present disclosure is to provide catalysts for oxidative coupling reaction of methane in which sodium tungstate is supported on a modified silica carrier.

Another aspect of the present disclosure is to provide a method for oxidative coupling reaction of methane using the catalysts for oxidative coupling reaction of methane.

In one aspect, the techniques disclosed herein provides catalysts for oxidative coupling reaction of methane comprising one or more carrier selected from the group consisting of a zeolite having a delaminated structure, titanium silicate-1 (TS-1), MCM-41, MCM-22 and ZSM-5; and sodium tungstate supported on the carrier.

In one exemplary embodiment, the zeolite having a delaminated structure may be a nanosheet zeolite.

In one exemplary embodiment, the zeolite having a delaminated structure may be one or more selected from the group consisting of pillared ITQ-1, delaminated ITQ-1 and ITQ-2.

In one exemplary embodiment, the pillared ITQ-1 carrier may be synthesized by adding cetyltrimethylammonium bromide (CTAB) and tetrapropyl ammonium hydroxide (TPAOH) to an ITQ-1 precursor and introducing tetraethyl orthosilicate (TEOS) thereto.

In one exemplary embodiment, the delaminated ITQ-1 carrier may be synthesized by adding cetyltrimethylammonium bromide (CTAB) and tetrapropyl ammonium hydroxide (TPAOH) to an ITQ-1 precursor and sonicating the mixture.

In one exemplary embodiment, the catalysts may further comprise a metal oxide supported on the carrier.

In one exemplary embodiment, the catalysts may further comprise from 0.1 to 5% by weight of a metal oxide relative to the total weight of the catalysts.

In one exemplary embodiment, the metal oxide may be an oxide of one or more selected from the group consisting of manganese (Mn), aluminum (Al), magnesium (Mg), zinc (Zn), copper (Cu), cobalt (Co), cerium (Ce), lanthanum (La), nickel (Ni), titanium (Ti), chromium (Cr) and lithium (Li).

In one exemplary embodiment, the catalysts may comprise from 1 to 10% by weight of sodium tungstate relative to the total weight of the catalysts.

In another aspect, the technology disclosed herein provides a method for oxidative coupling reaction of methane comprising adding the catalysts for oxidative coupling reaction of methane to methane to prepare a hydrocarbon compound comprising two or more carbon atoms from methane.

In one exemplary embodiment, the method may comprise the steps of: introducing a mixed gas comprising methane, oxygen and an inert gas into a reactor; and adding catalysts for oxidative coupling reaction of methane to the reactor to perform an oxidative coupling reaction of methane.

In one exemplary embodiment, the methane and oxygen may be mixed in a volume ratio of 1:10 to 10:1.

In one exemplary embodiment, the oxidative coupling reaction of methane may be performed at 700 to 900° C.

In one exemplary embodiment, the oxidative coupling reaction of methane may be performed at a gas hourly space velocity (GHSV) of 5,000 to 15,000 h$^-$.

One aspect of the present disclosure provides catalysts for oxidative coupling reaction of methane comprising sodium tungstate supported on a modified silica carrier.

Another aspect of the present disclosure provides a method for oxidative coupling reaction of methane, which allows to prepare a hydrocarbon compound comprising two or more carbon atoms from methane at a high yield by using the catalysts for oxidative coupling reaction of methane.

DETAILED DESCRIPTION OF THE PREFERRED EMBODIMENTS

Figure 1:
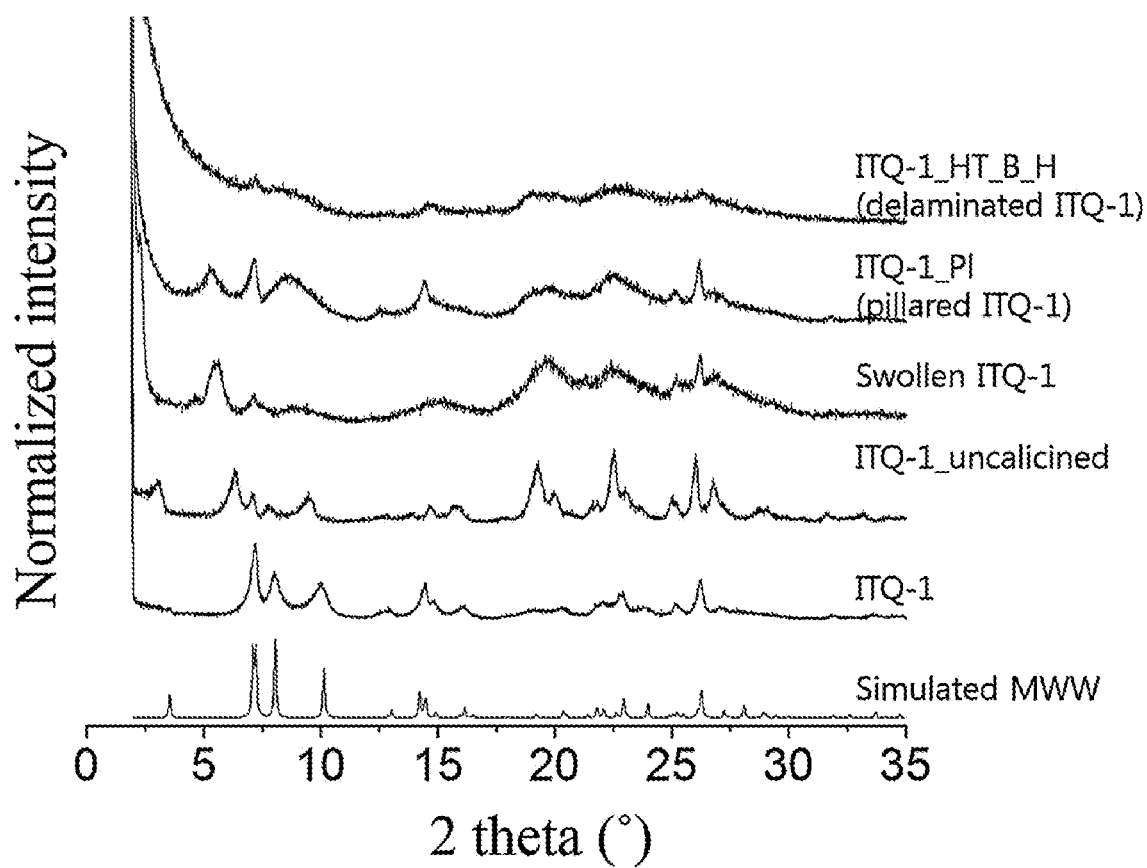
FIG. 1 shows the XRD structures of ITQ-1 zeolites synthesized in one example of the present disclosure.

Hereinafter, the present invention will be described in detail.

Based on the finding that the oxidative coupling reaction of methane proceeds very differently depending on the type of the carrier on which sodium tungstate is supported, the technology disclosed herein provides catalysts for oxidative coupling reaction of methane comprising sodium tungstate supported on a carrier, and which exhibits an excellent methane conversion rate and $C_{2+}$ hydrocarbon selectivity.

As used herein, the term "$C_2$ hydrocarbon compound" refers to a hydrocarbon compound having two carbon atoms.

As used herein, the term "$C_{2+}$ hydrocarbon compound" refers to a hydrocarbon compound having two or more carbon atoms.

In one aspect, the techniques disclosed herein provides catalysts for oxidative coupling reaction of methane comprising one or more carrier selected from the group consisting of a zeolite having a delaminated structure, silica gel, silica aerogel, ITQ-1, silicalite-1, fumed silica, titanium silicate-1 (TS-1), MCM-41, MCM-22 and ZSM-5; and sodium tungstate supported on the carrier.

In one exemplary embodiment, the zeolite having a delaminated structure may be a nanosheet zeolite.

Zeolite is a microporous crystal, the skeleton of which is composed of aluminum and silicon covalently bonded through oxygen. Zeolite is known to have more than 200 structures depending on the size, shape and connectivity of the micropores. The zeolite crystals can be prepared in various crystalline forms, and some zeolites can be obtained as a layered structure. These layered zeolites can be converted into various structures through post-synthesis treatment and may exhibit different effects in catalysis depending on the type of the resultant structure.

The zeolite having a delaminated structure as used herein refers to a crystalline zeolite whose layers are separated or separable from each other.

In one exemplary embodiment, the zeolite having a delaminated structure may be one or more selected from the group consisting of pillared ITQ-1, delaminated ITQ-1 and ITQ-2.

The carrier as used herein may be a commercially available material or may be prepared by a conventional method or by appropriately modifying a known method.

In one exemplary embodiment, the silica gel is an amorphous silicon oxide and may have a surface area of about 215 m$^2$/g.

In one exemplary embodiment, the silica aerogel is a mesoporous material composed of $SiO_2$ and may be prepared by supercritically drying the silica gel synthesized by the sol-gel method. For example, the silica aerogel may be an amorphous silica compound prepared by replacing the solvent of silica wet gel with supercritical carbon dioxide and drying the resultant.

In one exemplary embodiment, the ITQ-1 is a silicon oxide zeolite having an MWW structure and may be prepared by adding TMAdaOH, HMI, or both to a silica precursor and mixing the mixture with distilled water to perform hydrothermal synthesis. The MWW crystal structure is discussed in "Atlas of Zeolite Framework Types," 6th edition, 2007, which is incorporated herein by reference in its entirety. Known examples of molecular sieves having this structure include MCM-22 (Science, Vol. 264, 1910 (1994)) and ITQ-1 (Chem. Mater., Vol. 8, 2415(1996) and J. Phys. Chem. B, Vol. 102, 44(1998)). The main XRD peaks and the interplanar distances of MWW structure zeolite are shown in Table 1 below.

TABLE 1

| (hkl) | 2 theta (degree)* | d (Å) |
|---|---|---|
| (002) | 7.08 | 12.5 |
| (004) | 14.2 | 6.24 |
| (310) | 26.1 | 3.41 |

*2 theta values obtained using CuKα$_1$ source.

In one exemplary embodiment, the silica precursor as used herein may include one selected from the group consisting of colloidal silica, sodium metasilicate, lithium silicate, tetraethyl orthosilicate, fumed silica, and combinations thereof, although not limited thereto.

In one exemplary embodiment, the pillared ITQ-1 is a nanosheet zeolite synthesized by forming silica pillars between the layers of ITQ-1. It may be prepared by mixing an ITQ-1 precursor with CTAB and TPAOH and then introducing TEOS. Pillared ITQ-1 can be prepared by a conventional method of preparing MCM-36 from MCM-22 (P), but with ITQ-1 as a raw material (Maheshwari et al., *Journal of the American Chemical Society*, 2008, 130, 1507). The specific synthesis method is disclosed in Examples.

In one exemplary embodiment, the delaminated ITQ-1 is a nanosheet zeolite and may be prepared by adding CTAB and TPAOH to a precursor of ITQ-1 and sonicating the mixture. Delaminated ITQ-1 can be prepared by a conventional method of preparing ITQ-2 from MCM-22(P), but with ITQ-1 as a raw material (He et al., *Microporous and*

*Mesoporous Materials*, 1998, 25, 207). The specific synthesis method is disclosed in Examples.

In one exemplary embodiment, the silicalite-1 is a silicon oxide zeolite and may be prepared by mixing with TEOS, TPAOH, IPA and distilled water in a molar ratio of, for example, 1:0.36:4:19.2 and performing hydrothermal synthesis.

In one exemplary embodiment, the fumed silica is an amorphous silica oxide. It may have a surface area of about 200 m$^2$/g and may be synthesized by heating a silica precursor at high temperature.

In one exemplary embodiment, the TS-1 is a silicon titanium oxide zeolite and may be prepared by mixing TEOS, Ti(OBu)$_4$, TPAOH and distilled water in a molar ratio of, for example, 1:0.1:0.36:35 and performing hydrothermal synthesis.

In one exemplary embodiment, the TS-1 may have a Si/Ti ratio of 1-100.

In one exemplary embodiment, pillared ITQ-1 or delaminated ITQ-1 may be used as the carrier to significantly improve the methane conversion rate and C$_{2+}$ hydrocarbon selectivity.

In one exemplary embodiment, the pillared ITQ-1 carrier may be prepared by adding cetyltrimethylammonium bromide (CTAB) and tetrapropyl ammonium hydroxide (TPAOH) to an ITQ-1 precursor and introducing tetraethyl orthosilicate (TEOS).

In one exemplary embodiment, the delaminated ITQ-1 carrier may be synthesized by adding cetyltrimethylammonium bromide (CTAB) and tetrapropyl ammonium hydroxide (TPAOH) to an ITQ-1 precursor and sonicating the mixture.

In one exemplary embodiment, the catalysts may further comprise a metal oxide supported on the carrier to significantly improve the methane conversion rate and C$_{2+}$ hydrocarbon selectivity.

In one exemplary embodiment, the catalysts may comprise from 0.1 to 5% by weight, from 3 to 5% by weight, or from 1 to 3% by weight of a metal oxide relative to the total weight of the catalysts. In another exemplary embodiment, the catalysts may comprise 0.01% by weight or more, 0.1% by weight or more, 1% by weight or more, 2% by weight or more, 3% by weight or more, 4% by weight or more, or 5% by weight or more and 5% by weight or less, 4% by weight or less, 3% by weight or less, 2% by weight or less, or 1% by weight or less of a metal oxide relative to the total weight of the catalysts.

In one exemplary embodiment, the metal oxide may be an oxide of one or more selected from the group consisting of manganese (Mn), aluminum (Al), magnesium (Mg), zinc (Zn), copper (Cu), cobalt (Co), cerium (Ce), lanthanum (La), nickel (Ni), titanium (Ti), chromium (Cr) and lithium (Li).

In one exemplary embodiment, the metal oxide may be formed from a metal precursor.

In one exemplary embodiment, the metal precursor may be one or more selected from the group consisting of metal salt compounds, metal acetate compounds, metal halide compounds, metal nitrate compounds, metal hydroxide compounds, metal carbonyl compounds, metal sulfate compounds, and metal fatty acid salt compounds.

In one exemplary embodiment, the catalysts may comprise from 1 to 10% by weight, from 1 to 5% by weight, from 3 to 5% by weight, or from 1 to 3% by weight of sodium tungstate relative to the total weight of the catalysts. In another exemplary embodiment, the catalysts may comprise 0.01% by weight or more, 0.1% by weight or more, 1% by weight or more, 2% by weight or more, 3% by weight or more, 4% by weight or more, or 5% by weight or more and 10% by weight or less, 9% by weight or less, 8% by weight or less, 7% by weight or less, 6% by weight or less, 5% by weight or less, 4% by weight or less, 3% by weight or less, 2% by weight or less, or 1% by weight or less of sodium tungstate relative to the total weight of the catalysts.

In another aspect, the technology disclosed herein provides a method for oxidative coupling reaction of methane comprising adding the catalysts for oxidative coupling reaction of methane to methane to prepare a hydrocarbon compound comprising two or more carbon atoms from methane.

In one exemplary embodiment, the method may comprise the steps of: introducing a mixed gas comprising methane, oxygen and an inert gas into a reactor; and adding catalysts for oxidative coupling reaction of methane to the reactor to perform an oxidative coupling reaction of methane.

In one exemplary embodiment, the inert gas may be nitrogen.

In one exemplary embodiment, the methane and oxygen may be mixed in a volume ratio of 1:10 to 10:1.

In one exemplary embodiment, the method for oxidative coupling reaction of methane may be performed at 700 to 900° C. If the temperature is lower than 700° C., the oxidative coupling reaction of methane exhibits almost no activity. If the temperature is higher than 900° C., it may be difficult to operate the reactor due to the high temperature. Given the above aspect, it may be preferable to perform the oxidative coupling reaction of methane at a temperature of 700° C. or higher, 750° C. or higher, 775° C. or higher, 800° C. or higher, 850° C. or higher or 900° C. or higher and 900° C. or lower, 850° C. or lower, 800° C. or lower, 775° C. or lower, 750° C. or lower, or 700° C. or lower. For example, the method for oxidative coupling reaction of methane achieves excellent effects in terms of methane conversion rate and C$_{2+}$ hydrocarbon selectivity, when performed at 750 to 850° C., or 750 to 800° C., or 775 to 800° C.

In one exemplary embodiment, the method for oxidative coupling reaction of methane may be performed at a gas hourly space velocity (GHSV) of 5,000 to 15,000 h$^{-1}$.

In one exemplary embodiment, the C$_{2+}$ hydrocarbon compound may include one or more selected from the group consisting of ethane (C$_2$H$_6$), ethylene (C$_2$H$_4$), acetylene (C$_2$H$_2$), propane (C$_3$H$_8$) and propylene (C$_3$H$_6$).

The catalysts for oxidative coupling reaction of methane disclosed herein pull oxygen to convert it into an oxygen radical, convert methane to a methyl radical using it, and then mediates the coupling reaction. In this process, the catalysts help to transfer oxygens and electrons and activate methane to accelerate the oxidative coupling reaction of methane. In addition, the catalysts enable to prepare a C$_{2+}$ hydrocarbon compound with a high yield through the oxidative coupling reaction of methane.

The step of preparing a C$_{2+}$ hydrocarbon compound may be a step of raising the temperature of the reactor to a predetermined reaction temperature to perform the oxidative coupling reaction of methane, which may result in the production of C$_{2+}$ hydrocarbon compounds in which a part or all of the methane is coupled.

In one exemplary embodiment, the reactor is a continuous reactor, and it may comprise a reactor filled with catalysts and zirconia beads, a portion for introducing a gas mixture comprising methane, oxygen, and an inert gas into the reactor, a furnace for adjusting the temperature of the reactor, a water trap, and a gas chromatography system for detecting a product.

Figure 2:
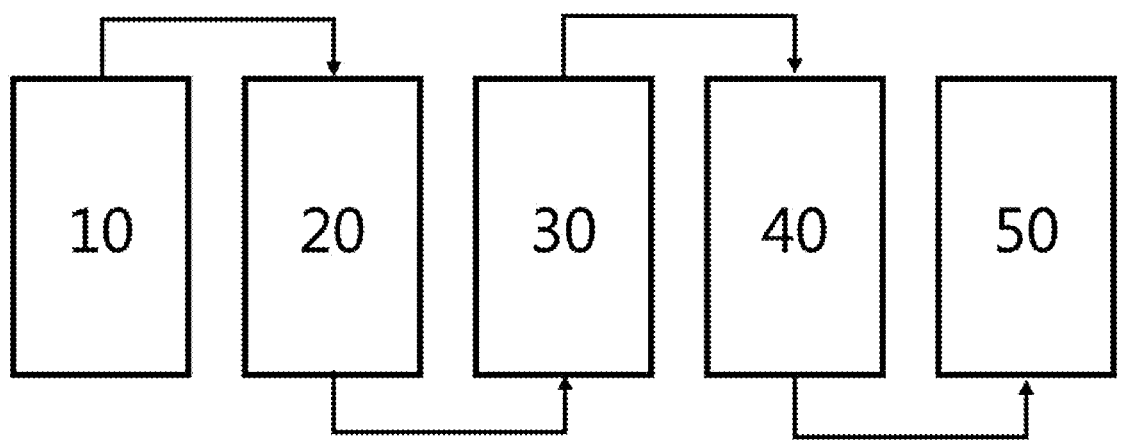
FIG. 2 schematically shows the configuration of a continuous reactor for oxidative coupling reaction of methane used in the production of $C_{2+}$ hydrocarbon compounds according to one example of the present disclosure.

FIG. 2 shows a continuous reactor that can be used in one example of the present disclosure.

In one exemplary embodiment, the continuous reactor may comprise a storage device 10 for storing methane, oxygen, and an inert gas, a mixing device 20 for mixing methane, oxygen, and an inert gas, a quartz tube reactor 30 connected to a heating device, a cooling device 40 for cooling and collecting the product after reaction, and a gas chromatography device 50 for analyzing the final product.

Hereinafter, the present invention will be described in more detail with reference to examples. It should be apparent to those skilled in the art that these examples are for illustrative purposes only and that the scope of the present invention is not construed as being limited by these examples.

Example 1

Preparation of Carrier (1) ITQ-1

1.125 g of fumed silica, 3.84 mL of trimethyladamantylammonium hydroxide (TMAdaOH), 0.6819 mL of hexamethylene imine (HMI) (either TMAdaOH or HMI may be used alone) and 14.82 g of water were mixed and hydrothermal synthesis was performed at 150° C. and 60 rpm for 72 hours. Then, vacuum filtering was performed several times to remove surfactants and obtain a solid. This solid is referred to herein as ITQ-1(P). ITQ-1(P) was calcined at 400° C. to synthesize ITQ-1.

(2) Silica Gel

Silica gel was obtained from Alfa Aesar.

(3) Silica Aerogel 60.1 mL of methanol and 22.8 mL of tetraethyl orthosilicate (TEOS) were mixed for 20 minutes, and then 0.0687 mL of ammonia solution was added and mixed for 30 minutes. After 30 minutes, 7.2 ml of distilled water was added and mixed for about 1 hour. 1 ml of a solution prepared by mixing ammonium fluoride in methanol at a molar ratio of 1:99 was introduced dropwise into the sol solution for gelation. The formed gel was aged for 1 to 3 days and then subjected to $CO_2$ supercritical drying (2000 psig, 70° C.). Finally, the resultant was calcined at 500° C. for 6 hours to obtain a silica aerogel (ramping rate: 1° C./min).

(4) MCM-41

MCM-41 (MCM is an abbreviation of Mobil Composition of Matter) is a material having a structure in which straight-line pores with a certain size are arranged in a hexagonal arrangement, i.e., a honeycomb arrangement, on a silica plate. In this Example, MCM-41 was a mesoporous silicon oxide having a pore size of 2.1 to 2.7 nm and a surface area of about 1,000 m$^2$/g. It was obtained from Sigma-Aldrich.

(5) ITQ-2

ITQ-2 is a zeolite having the same structure as pillared ITQ-1, but with Al added. First, 29 g of a 20% by weight aqueous solution of MCM-22(P), 105 g of a 29% by weight aqueous solution of hexadecyltrimethylammonium bromide (CTAB), and 33 g of a 40% by weight aqueous solution of tetrapropyl ammonium hydroxide (TPAOH) were mixed and stirred at 80° C. for 16 hours. Thereafter, the mixture was sonicated using ultrasonic waves of 50 W and 40 kHz for 1 hour. A small amount of hydrochloric acid was added thereto to adjust the pH to 2 or less, followed by centrifugation to obtain a solid product. The solid product was calcined at 540° C. to obtain ITQ-2.

(6) MCM-22

MCM-22 is a zeolite having the same structure as ITQ-1, but with Al added. First, 0.23 g of sodium aluminate (56% $Al_2O$, 37% $Na_2O$, Carlo Erba, Milan) and 0.81 g of sodium hydroxide were dissolved in 103.45 g of distilled water. Then, the mixture was mixed with 6.35 g of HMI and 7.86 g of silica Aerosil. The mixture was stirred at room temperature for 30 minutes and then hydrothermal synthesis was performed at 135° C. for 11 days under argon atmosphere. The resultant solid product was vacuum filtered and washed with distilled water until the pH was less than 9. The filtered solid product is referred to herein as MCM-22(P). MCM-22(P) was calcined at 400° C. to synthesize MCM-22.

(7) Pillared ITQ-1

1 g of swollen ITQ-1(P) and 5 g of tetraethyl orthosilicate (TEOS) were mixed and then heated in an oil bath at 78° C. for 25 hours with stirring under argon atmosphere. The resultant mixture was centrifuged several times to obtain a solid. 0.5 g of the solid and 5 g of water were mixed and hydrolysis was performed at 140° C. for 6 hours. At this time, the pH was adjusted to 8. Finally, the solid was calcined at 450° C. for 6 hours to synthesize pillared ITQ-1.

(8) Delaminated ITQ-1

1.125 g of ITQ-1(P), 11 g of tetrapropyl ammonium hydroxide (TPAOH, 40% solution), 10.15 g of cetyltrimethylammonium bromide (CTAB) and 32.1 g of water were mixed and stirred at 80° C. for 16 hours to cause swelling. The resultant is referred to herein as Swollen ITQ-1(P). Thereafter, the mixture in which the swelling occurred was sonicated for 60 minutes and then the pH was adjusted to 2. The resultant mixture was centrifuged several times to obtain a solid. The solid was calcined at 550° C. for 12 hours to synthesize delaminated ITQ-1.

(9) ZSM-5

ZSM-5 is a zeolite having a structure in which Ti of TS-1 is substituted with Al. ZSM-5 was obtained from Alfa aesar.

(10) Silicalite-1

16.1 mL of TEOS, 5 mL of isopropyl alcohol (IPA), 11.6 mL of TPAOH (20% solution) and 18.1 mL of water were mixed and aged at 25° C. for 72 hours. Then, hydrothermal synthesis was performed at 175° C. for 24 hours. Vacuum filtering was performed several times to remove surfactants and obtain a solid. The solid was calcined at 400° C. to synthesize silicalite-1.

(11) TS-1

15 g of TEOS, 0.75 g of Ti(OBu)$_4$, 23 g of TPAOH (20% solution) and 23 g of water were mixed and heated at 60° C. for 1 hour. Then, hydrothermal synthesis was performed at 160° C. for 24 hours. Vacuum filtering was performed several times to remove surfactants and obtain a solid. The solid was calcined at 400° C. to synthesize TS-1.

(12) Fumed Silica

Fumed silica was obtained from Sigma-Aldrich.

Example 2

Preparation of Catalyst

Catalysts for oxidative coupling reaction of methane in which manganese oxide as the metal oxide and sodium tungstate were supported on a carrier were prepared using the carriers prepared in Example 1.

0.1280 g of sodium tungstate dihydrate and 0.1309 mL of manganese nitrate hexahydrate were mixed with an aqueous solution prepared by mixing 2 g of each carrier and 70 g of distilled water and stirring them for 30 minutes. The mixture was then stirred for about 3 hours. Thereafter, the aqueous solution was dried at 105° C. for 16 hours and then calcined at 800° C. for 5 hours to prepare the respective catalysts for oxidative coupling reaction of methane.

Test Example 1

Oxidative Coupling Reaction of Methane by Catalysts Using a Modified Silica Carrier Oxidative coupling reaction of methane was performed using the catalysts prepared in Example 2 and a continuous reactor. The reaction temperature was maintained at 750 to 850° C. (reaction conditions: time on stream (TOS)=0.5 to 3 hours, total flow rate=30 mL/min, volume ratio of methane:oxygen:nitrogen=15:7.5:7.5, GHSV=10,000 h$^{-1}$, catalyst volume=0.18 mL). The gas mixture obtained after the reaction was analyzed using gas chromatography.

Table 2 below shows the results of reactions at 800° C. with the various catalysts prepared in Example 2. The $C_{2+}$ hydrocarbon includes ethane ($C_2H_6$), ethylene ($C_2H_4$), propane ($C_3H_8$), and propylene ($C_3H_6$).

TABLE 2

| Catalyst | Methane conversion rate (%) | $C_{2+}$ hydrocarbon selectivity (mol %) | $C_{2+}$ hydrocarbon yield (mol %) | Ratio of ethylene/ethane (mol/mol) |
| --- | --- | --- | --- | --- |
| Na$_2$WO$_4$/Mn/ITQ-1 | 44.9 | 48.6 | 21.8 | 2.90 |
| Na$_2$WO$_4$/Mn/Silica gel | 45.4 | 52.1 | 23.6 | 2.60 |
| Na$_2$WO$_4$/Mn/Silica aerogel | 44.4 | 51.6 | 22.9 | 2.84 |
| Na$_2$WO$_4$/Mn/MCM-41 | 42.9 | 44.0 | 18.9 | 2.77 |
| Na$_2$WO$_4$/Mn/ITQ-2 | 42.9 | 47.7 | 20.5 | 2.60 |
| Na$_2$WO$_4$/Mn/MCM-22 | 21.6 | 33.8 | 7.29 | 1.33 |
| Na$_2$WO$_4$/Mn/Pillared ITQ-1 | 47.6 | 55.7 | 26.5 | 2.08 |
| Na$_2$WO$_4$/Mn/Delaminated ITQ-1 | 49.0 | 55.7 | 27.3 | 2.04 |
| Na$_2$WO$_4$/Mn/ZSM-5 | 28.7 | 31.7 | 9.10 | 1.98 |
| Na$_2$WO$_4$/Mn/Silicalite-1 | 42.0 | 44.2 | 18.6 | 2.67 |
| Na$_2$WO$_4$/Mn/TS-1 | 40.3 | 43.0 | 17.3 | 2.59 |
| Na$_2$WO$_4$/Mn/Fumed silica | 41.9 | 46.2 | 19.3 | 2.77 |

The result showed that the catalysts prepared in Example 2 can increase the $C_{2+}$ hydrocarbon yield by smoothly performing the oxidative coupling reaction of methane. In addition, it was confirmed that the oxidative coupling reaction of methane may proceed differently depending on the type of the carrier on which sodium tungstate is supported. Specifically, the catalysts using silica gel, silica aerogel, MCM-41, ITQ-2, ITQ-1, pillared ITQ-1, delaminated ITQ-1, silicalite-1, fumed silica and TS-1 as the carrier were found to exhibit a very excellent methane conversion rate and $C_{2+}$ hydrocarbon selectivity.

Particularly, it was found that a sodium tungstate catalyst using as the carrier a delaminated zeolite, for example, pillared ITQ-1 or delaminated ITQ-1 significantly increase the methane conversion rate and $C_{2+}$ hydrocarbon selectivity and thereby remarkably facilitate the oxidative coupling reaction of methane. Specifically, a sodium tungstate catalyst using delaminated ITQ-1 as the carrier was found to significantly increase the methane conversion rate and $C_{2+}$ hydrocarbon selectivity, resulting in the increase of $C_{2+}$ hydrocarbon yield up to 27.3 mol %. Thus, it was confirmed that the catalyst enables to produce $C_{2+}$ hydrocarbon compounds efficiently at a high yield.

While specific embodiments of the present invention have been described, those skilled in the art will appreciate that these specific embodiments are merely preferred embodiments and that the scope of the present invention is not limited thereby. Thus, the substantial scope of the present invention should be defined by the appended claims and their equivalents.

What is claimed is:

1. Catalysts for oxidative coupling reaction of methane comprising:
   one or more carrier selected from the group consisting of pillared ITQ-1 and delaminated ITQ 1;
   sodium tungstate supported on the carrier; and
   a metal oxide supported on the carrier,
   wherein the catalysts for oxidative coupling reaction of methane increases methane conversion rate and $C_{2+}$ hydrocarbon selectivity as compared to ITQ-1 which is not pillared or delaminated.

2. The catalysts for oxidative coupling reaction of methane according to claim 1,
   wherein the catalysts comprises from 0.1 to 5% by weight of a metal oxide relative to the total weight of the catalysts.

3. The catalysts for oxidative coupling reaction of methane according to claim 1,
   wherein the metal oxide is an oxide of one or more selected from the group consisting of manganese (Mn), aluminum (Al), magnesium (Mg), zinc (Zn), copper (Cu), cobalt (Co), cerium (Ce), lanthanum (La), nickel (Ni), titanium (Ti), chromium (Cr) and lithium (Li).

4. The catalysts for oxidative coupling reaction of methane according to claim 1,
   wherein the catalysts comprise from 1 to 10% by weight of sodium tungstate relative to the total weight of the catalysts.

5. A method for oxidative coupling reaction of methane comprising:
   adding catalysts for oxidative coupling reaction of methane to methane and to prepare a hydrocarbon compound comprising two or more carbon atoms from the methane,
   wherein the catalysts for oxidative coupling reaction of methane comprises
   one or more carrier selected from the group consisting of pillared ITQ-1 and delaminated ITQ 1;
   sodium tungstate supported on the carrier; and
   a metal oxide supported on the carrier,
   wherein the catalysts for oxidative coupling reaction of methane increases methane conversion rate and $C_{2+}$ hydrocarbon selectivity as compared to ITQ-1 which is not pillared or delaminated.

6. The method for oxidative coupling reaction of methane according to claim 5,
   wherein the catalysts comprise from 0.1 to 5% by weight of the metal oxide relative to the total weight of the catalysts.

7. The method for oxidative coupling reaction of methane according to claim 5,
   wherein the metal oxide is an oxide of one or more selected from the group consisting of manganese (Mn), aluminum (Al), magnesium (Mg), zinc (Zn), copper (Cu), cobalt (Co), cerium (Ce), lanthanum (La), nickel (Ni), titanium (Ti), chromium (Cr) and lithium (Li).

8. The method for oxidative coupling reaction of methane according to claim 5,
   wherein the catalysts comprise from 1 to 10% by weight of sodium tungstate relative to the total weight of the catalysts.

9. The method for oxidative coupling reaction of methane according to claim 5,
   wherein the method comprises the steps of:
   introducing a mixed gas comprising methane, oxygen and an inert gas into a reactor; and adding catalysts for oxidative coupling reaction of methane to the reactor to perform an oxidative coupling reaction of methane.

10. The method for oxidative coupling reaction of methane according to claim 9,
    wherein the methane and oxygen are mixed in a volume ratio of 1:10 to 10:1.

11. The method for oxidative coupling reaction of methane according to claim 9,
    wherein the oxidative coupling reaction of methane is performed at 700 to 900° C.

12. The method for oxidative coupling reaction of methane according to claim 9,
    wherein the oxidative coupling reaction of methane is performed at a gas hourly space velocity (GHSV) of 5,000 to 15,000 $h^{-1}$.

* * * * *